(12) United States Patent
Sixto, Jr. et al.

(10) Patent No.: US 9,474,558 B2
(45) Date of Patent: *Oct. 25, 2016

(54) BONE PLATE WITH SCREW HOLE ARRANGEMENT

(71) Applicant: Biomet C.V., Gibraltar (GI)

(72) Inventors: Robert Sixto, Jr., Miami, FL (US); Juergen A. Kortenbach, Miami Springs, FL (US); Andrea Suarez, Miami, FL (US)

(73) Assignee: Biomet C.V., Gibraltar (GI)

( * ) Notice: Subject to any disclaimer, the term of this patent is extended or adjusted under 35 U.S.C. 154(b) by 308 days.

This patent is subject to a terminal disclaimer.

(21) Appl. No.: 14/041,437

(22) Filed: Sep. 30, 2013

(65) Prior Publication Data

US 2014/0031879 A1    Jan. 30, 2014

Related U.S. Application Data

(63) Continuation of application No. 13/313,350, filed on Dec. 7, 2011, now Pat. No. 8,632,574.

(51) Int. Cl.
*A61B 17/80* (2006.01)
*A61B 17/86* (2006.01)

(52) U.S. Cl.
CPC ....... *A61B 17/8052* (2013.01); *A61B 17/8057* (2013.01); *A61B 17/8061* (2013.01); *A61B 17/8605* (2013.01)

(58) Field of Classification Search
CPC .......... A61B 17/8057; A61B 17/8052; A61B 17/8061; A61B 17/8605
See application file for complete search history.

(56) References Cited

U.S. PATENT DOCUMENTS

| 5,259,398 | A | | 11/1993 | Vrespa | |
|---|---|---|---|---|---|
| 5,709,686 | A | * | 1/1998 | Talos | A61B 17/8057 606/280 |
| 6,129,730 | A | | 10/2000 | Bono et al. | |
| 6,786,909 | B1 | * | 9/2004 | Dransfeld | A61B 17/8052 606/280 |
| 7,951,176 | B2 | * | 5/2011 | Grady, Jr. | A61B 17/746 606/280 |

(Continued)

FOREIGN PATENT DOCUMENTS

| EP | 2389884 A1 | 11/2011 |
|---|---|---|
| WO | WO-2013085835 A1 | 6/2013 |

OTHER PUBLICATIONS

"European Application Serial No. 12812761.0, Examination Notification Art. 94(3) mailed Apr. 1, 2015", 4 pgs.

(Continued)

*Primary Examiner* — Christian Sevilla
(74) *Attorney, Agent, or Firm* — Schwegman Lundberg & Woessner, P.A.

(57) ABSTRACT

An orthopedic screw system includes a screw with a locking head that can both lockingly engage in a fixed angle threaded screw hole to secure a plate to a bone without compression, and non-lockingly engage at a compression screw hole to provide compression between the plate and the bone. The structure of the system is particularly well adapted to plates and screw of small dimensions, such as screws smaller than 3.5 mm and is capable of providing high compressive force, on the order of 120 lbs of axial load, without significant plastic deformation between the screw and plate. Further, the screw holes are structured for arrangement in tight clusters on the bone plate, thereby facilitating a compact design on the bone plate.

30 Claims, 5 Drawing Sheets

(56) References Cited

U.S. PATENT DOCUMENTS

| | | |
|---|---|---|
| 8,496,690 B2 | 7/2013 | Sixto et al. |
| 8,632,574 B2 * | 1/2014 | Kortenbach ....... A61B 17/8057 606/280 |
| 2004/0193164 A1 * | 9/2004 | Orbay ................ A61B 17/8057 606/281 |
| 2005/0192578 A1 * | 9/2005 | Horst .................. A61B 17/863 606/281 |
| 2006/0264946 A1 * | 11/2006 | Young ................ A61B 17/1728 606/915 |
| 2008/0132960 A1 | 6/2008 | Weaver et al. |
| 2009/0312803 A1 | 12/2009 | Austin et al. |
| 2009/0318921 A1 * | 12/2009 | White ................ A61B 17/8085 606/70 |
| 2010/0069969 A1 | 3/2010 | Ampuero et al. |
| 2011/0071572 A1 | 3/2011 | Sixto et al. |
| 2011/0295325 A1 | 12/2011 | Wagner et al. |
| 2015/0209091 A1 * | 7/2015 | Sixto, Jr. ............ A61B 17/8057 606/289 |

OTHER PUBLICATIONS

U.S. Appl. No. 12/884,242, filed Sep. 17, 2010, Applicant: Robert Sixto et al.

* cited by examiner

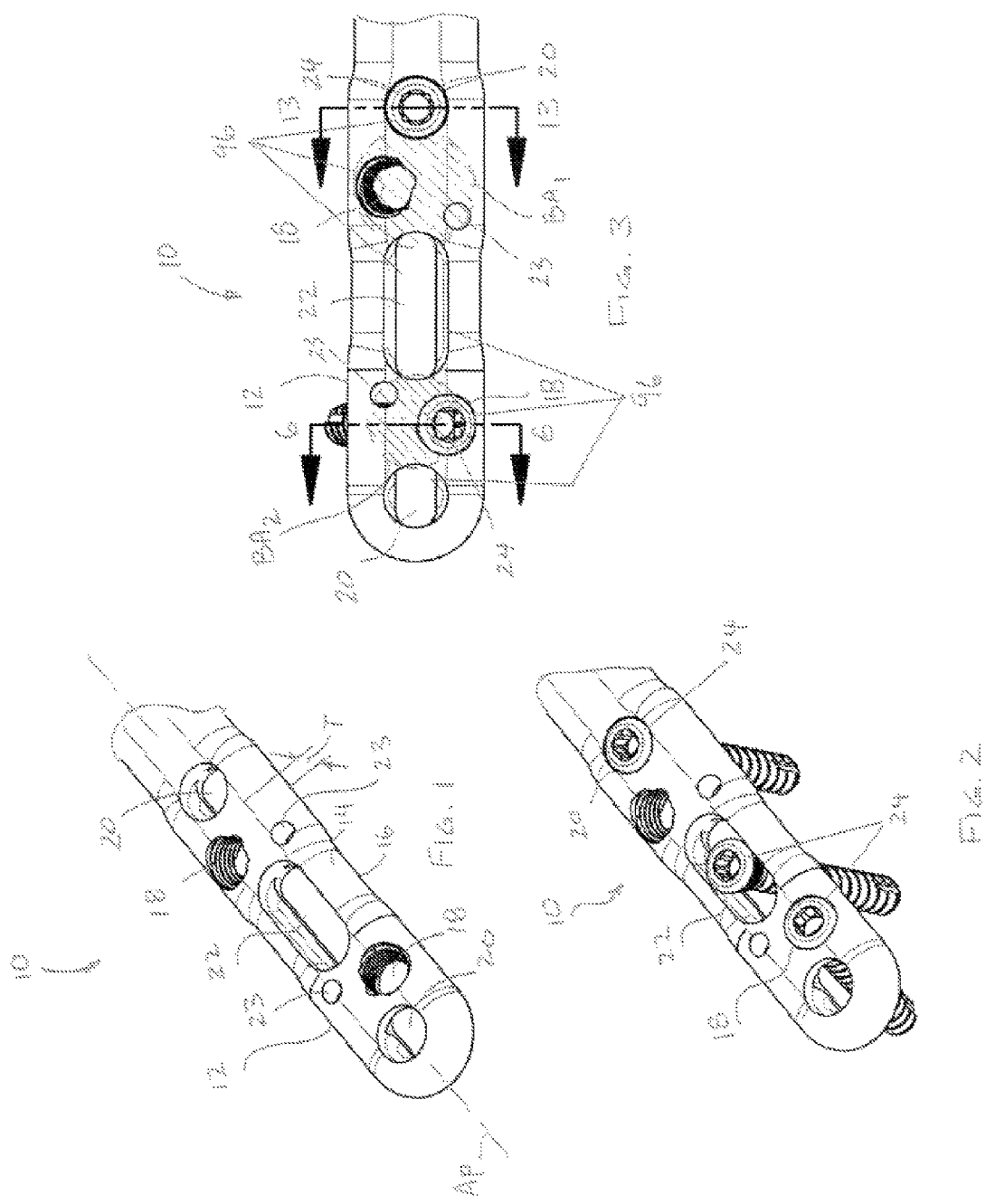

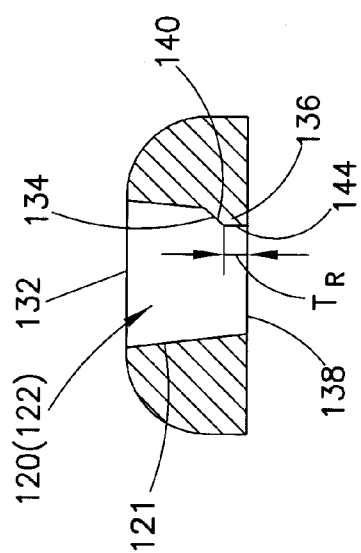
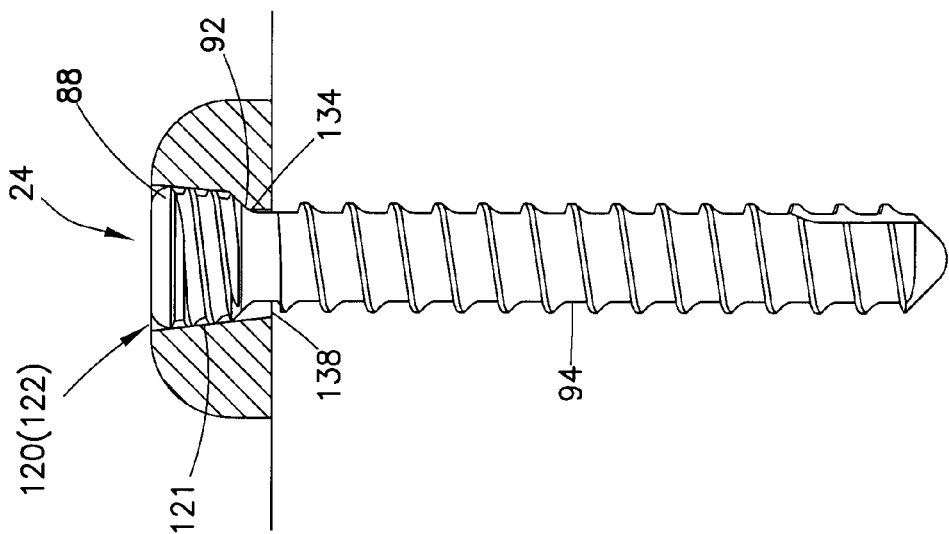
FIG. 15
FIG. 16

BONE PLATE WITH SCREW HOLE ARRANGEMENT

CROSS-REFERENCE TO RELATED APPLICATION

This application is a continuation of U.S. Ser. No. 13/313,350, filed Dec. 7, 2011, which is hereby incorporated by reference herein in its entirety.

BACKGROUND OF THE INVENTION

1. Field of the Invention

The present invention relates to surgery. More particularly, the invention relates to orthopedic systems, including plates and screws therefor.

2. State of the Art

Bone plates can be used to repair traumatic bone fractures. The plates are positioned on the bone and screws are inserted through holes in the plate and into underlying bone to secure the plate relative to the bone to aid in healing.

Various options are provided for coupling the plate to the bone. At specific locations on the bone and relative to a fracture it may be appropriate to use compressive fixation in which a compressive screw is inserted into a screw hole in the plate and the underlying bone to secure the plate to the bone with compression. Such compression screw holes are often provided to a plate in a combination of round and oblong screw holes. An oblong screw hole allows the plate to be positioned in a trial location on the bone. A hole is then drilled through a location within the oblong screw hole and a compressive screw is advanced through the hole into a preferably slight contact with the plate. The plate may then be moved relative to the screw into a final position before the compressive screw is advanced to axially load the plate against the bone. In addition, round non-threaded screw holes in the plate are provided to receive compressive screws at defined locations relative to the plate and the underlying bone. Compression screw holes and screws can be provided in varieties that permit both fixed angle and multi-angular approaches for attachment of the plate to the underlying bone.

At other locations relative to the fracture it may be appropriate to use a locking screw that is inserted into the plate and the underlying bone and then locked in relative to the plate with the locking screw retaining bone fragments in relation to the plate; such a screw does not apply significant compressive force between the plate and the bone. Locking screws often couple to the plate by a threaded engagement between external threads on the head of the screw and internal threads formed in a screw hole.

Further, the requirements of a bone plate system that is of reduced dimension and thickness profile to accommodate smaller bones necessitates additional considerations. Providing a reduced profile bone plate system allows the plate and its associated screws to be used on bones of the extremities which are difficult to treat. This is especially important for plates used to repair bone fractures where the bone has little protection by overlying soft tissues and is highly vulnerable, for example, to accidental bumping as the fracture heals. Development of very thin, anatomically conforming bone plates has created new challenges related to plate-to-bone attachment. More specifically, improved designs for screw systems are needed to reduce the hardware that protrudes above the top surface of the plate and irritates and/or inflames the overlying tissues. Further, smaller screws are weaker, particularly at the screw head around the driver socket, and prone to failure when torqued to apply axially loading.

Regardless of plate and screw size, there is a drive toward reducing the inventory of components necessary to complete a plating procedure. However, each of the compression screw holes and locking screw holes generally is structured to receive a different type of screw, particularly having different structure at the head of the screw. The head of the non-locking compression screw is structure for application of axial loads, whereas the head of the locking screw is structured to mechanically couple the screw directly to the plate. Moreover, each type of screw is provided in several lengths within the surgical set. This requires a level of inventory control that is difficult to maintain. Alternatively, with respect to prepackaged systems that are intended to contain all necessary components for completing a plating procedure, the sheer number of components can lead to significant and expensive waste; this is untenable where health care costs are being managed.

Previously there has been some work to reduce the number of screws required to be included in a bone plate system. By way of example, co-owned US Pub. No. 20100069969 discloses a system that converts locking screws to compressive screws by attaching a washer element to the head of the locking screws to increase the effective surface area of the screw head that applies the axial compressive load against the plate. While the number of required screws is decreased by such a system, the system nevertheless requires the inclusion of washers and specialized instrumentation to couple the washers to the screw heads.

SUMMARY OF THE INVENTION

An orthopedic screw system is provided that includes a plate with at least one tapered and threaded locking screw hole and at least one non-threaded compression screw hole which is in the form of a round hole or an oblong hole. The compression screw hole has an upper opening with a first diameter, a lower portion with a lowermost opening with a smaller second diameter, and a screw seat between the upper opening and lower portion.

The system also includes a single type of bone screw that can be used in either type of screw hole to (i) mechanically lock relative to the plate when the screw is inserted into the threaded locking hole or (ii) axially load the plate relative to the bone when the screw is inserted into the compression screw hole. The screw has a head and a shaft. The head includes conically tapered external threads. A bearing annulus smaller than the head thread diameter is defined at the interface of the head and the shaft. The shaft has bone engaging threads defining a minor diameter at the troughs and a major diameter at the crests. The major diameter is larger than the second diameter of the compression screw hole, such that the shaft must be rotationally threaded through the lowermost opening of the compression screw hole to be longitudinally advanced therethrough. The bearing annulus is configured to present a large surface area for the given diameter of the annulus and supports a high axial load on the screw seat of the compression holes. Further, the bearing annulus displaces the axially loads from weaker portions of the screw head which could otherwise be subject to plastic deformation.

The system allows a single type of screw to be used in association with a plate to provide for axial compression loading in compression holes and locking fixation to the plate in locking holes. The system is particularly well adapted to plates and screws of small dimensions, and is capable of applying high compression loads between the screws and plate at the compression holes without significant plastic deformation.

Furthermore, the system reduces the inventory of components required for a surgical plating procedure. Moreover, the system simplifies the procedure, as the surgeon is able to use the same screw regardless of the type of screw fixation required.

BRIEF DESCRIPTION OF THE DRAWINGS

FIG. 1 is a perspective view of a portion of a bone plate according to the invention.

FIG. 2 is a view similar to FIG. 1 in which bone screws are received in screw holes of the bone plate.

FIG. 3 is a top view of the portion of the bone plate.

FIG. 15 is a cross-section view transverse to the longitudinal axis of the bone plate, showing an alternative embodiment of a compression screw hole according to the invention.

FIG. 16 is a partial section view showing the bone screw inserted into the compression screw hole shown in FIG. 15.

DETAILED DESCRIPTION OF THE PREFERRED EMBODIMENTS

Figure 4:
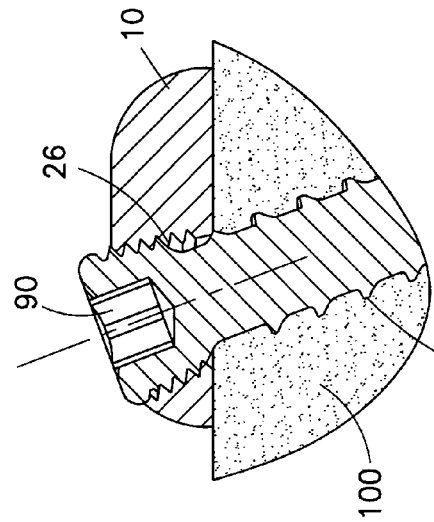
FIG. 4 is a top view of a small portion of the bone plate showing a threaded screw hole according to the invention.

Turning now to FIG. 1, a bone plate 10 according to the invention is shown. The plate 10 shown has a straight portion 12 defining a longitudinal axis $A_P$. The straight portion 12 of the plate may be a portion of a diaphyseal plate for placement along the diaphysis of a long bone of an upper or lower extremity. Alternatively, the straight portion 12 may be one end of a metaphyseal plate for use at the end of a long bone. As another alternative, the straight portion 12 may be a segment of any other plate having an elongate portion. Further, the plate 10 may be manufactured to assume other shapes that are suitable for use on various bones throughout the human body. The plate 10 is manufactured from metal, and more preferably machined from a solid block of titanium or titanium alloy.

The plate 10 has an upper surface 14, a bone contacting lower surface 16 and a thickness T defined between the upper and lower surfaces 14, 16. A plurality of screw holes 18, 20, 22, described below, extend between the upper and lower surfaces 14, 16. In addition to the screw holes, the plate optionally includes a plurality of significantly smaller and preferably cylindrical holes 23 that are sized to closely receive respective K-wires for temporary fixation during an implantation procedure. Referring to the screw holes, the plate is shown to include three types of screw holes: a threaded round locking hole 18, a non-threaded round compression hole 20, and a non-threaded oblong compression hole 22, each described further below. With respect to FIGS. 2 and 3, a screw 24, described in more detail below, is shown inserted within each of the screw holes 18 and 20. As will also be described, such same screw 24 can also be inserted in screw hole 22. In accord with the invention, the screw 24 regardless of the hole into which it is inserted has a common head and shaft design of common dimensions.

Figure 5:
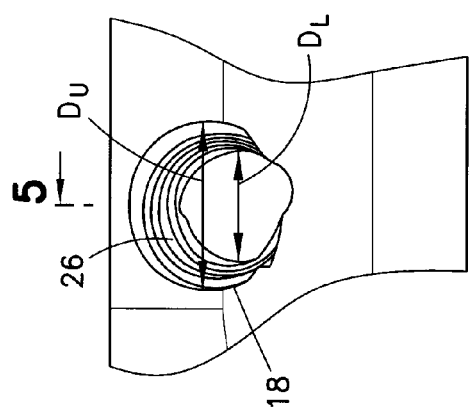
FIG. 5 is a section view of the bone plate along line 5-5 in FIG. 4.

Referring to FIGS. 1, 4 and 5, the threaded screw hole 18 has threads 26 helically arranged about its interior, and the hole is preferably substantially uniform about its internal circumference. The hole 18 is tapered so as to have an upper opening 28 at or adjacent the upper surface 14 of the plate with a diameter $D_U$ larger than a diameter $D_L$ at a lower opening 30 at or adjacent the lower surface 16 of the plate.

Figure 7:
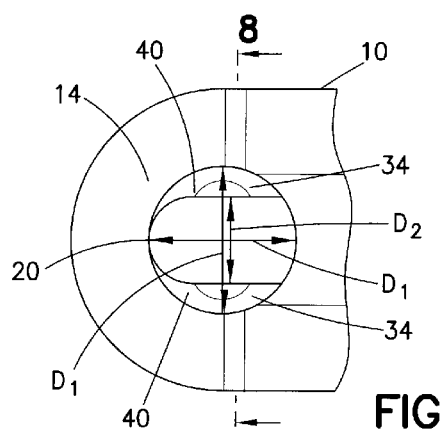
FIG. 7 is a top view of a small portion of the bone plate showing a round compression screw hole according to the invention.
Figure 8:
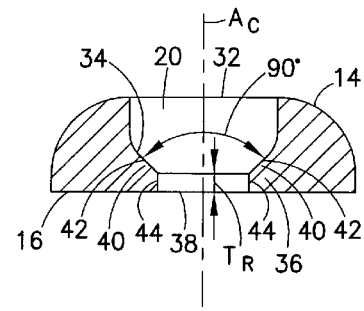
FIG. 8 is a section view of the bone plate across line 8-8 in FIG. 7.

Turning now to FIGS. 1 and 7 and 8, according to a first embodiment of the invention, the round compression screw hole 20 has an upper opening 32 at or adjacent the upper surface 14 of the plate 10 with a first diameter $D_1$ in each of two orthogonal directions and a lower opening 38 is provided at or adjacent the lower surface 16 of the plate with a smaller second diameter $D_2$ in one direction and the first diameter $D_1$ in a direction orthogonal to the second diameter $D_2$. With reference back to FIG. 4, the first diameter $D_1$ is preferably larger than the diameter $D_U$ of the upper opening of the threaded screw hole. The second diameter $D_2$ is preferably smaller than the diameter $D_L$ of the lower opening of the threaded screw hole 18. The screw hole 20 has a central axis $A_C$ extending through the centers of the upper and lower openings 32, 38.

Turning back to FIGS. 7 and 8, two parallel rails 40 recessed relative to the upper opening 38 extend across the screw hole. The upper surfaces 42 of the rails 40 are angled relative to each other at approximately 60°-90° and together define a screw seat 34. Vertically extending walls 44 of the rails 40 define a lower portion 36 of the screw hole and have a thickness $T_R$ extending in the same direction as the central axis of the compression screw hole 20. In the first embodiment, the rails 40 extend parallel to the longitudinal axis $A_P$ of the plate 10 (FIG. 1).

According to the first embodiment of the invention, the oblong compression screw hole 22 is substantially similar to the round compression screw hole, but extended in diameter; i.e., length, along the dimension in which the rails extend; that is, the screw hole 22 does not have the same $D_1$ diameter at two relatively orthogonal directions. For clarity of the following description, reference numerals which refer to elements similar to screw hole 20 are offset by 20 in screw hole 22. In accord therewith, screw hole 22 has an upper opening 52 with first major diameter $D_{M1}$ and a first minor diameter $D_{m1}$, and a lower opening or slot 58 with a second major diameter $D_{M2}$ and a second minor diameter $D_{m2}$. The first and second major diameters $D_{M1}$ and $D_{M2}$ are preferably of a common dimension, with the rails 60, and thus the seat 54, extending on laterally opposite sides of the first and second major diameters $D_{M1}$ and $D_{M2}$, but not at the ends of the first and second major diameters. The second minor diameter $D_{m2}$ is smaller than the first minor diameter $D_{m1}$.

Rails 60 extend lengthwise along the screw hole 22, parallel to but on opposite sides of the second major diameter $D_{m2}$, and in the first embodiment parallel to the longitudinal axis $A_P$ of the plate. As with the round compression screw hole 20, upper surfaces 62 of the rails 60 define a screw seat 64, and vertically extending walls 64 of the rails 60 define a lower portion 56 of the screw hole having the same thickness $T_R$. The first and second minor diameters $D_{m1}$ and $D_{m2}$ of the oblong screw hole 22 preferably correspond exactly in dimension to the first and second diameters $D_1$ and $D_2$ of the round compression screw hole 20.

Referring to FIGS. 1-3, the locking and compression holes 18, 20, 22 may be situated along the longitudinal axis $A_P$, offset from the longitudinal axis, or provided in a combination of both on-axis and off-axis locations. In the embodiment shown in FIG. 1, the compression screw holes 20, 22 are situated in alignment with the longitudinal axis $A_P$, whereas the threaded locking holes 18 are situated offset from the longitudinal axis. Further, referring to FIG. 5, the threaded locking holes 18 are oriented along an axis $A_H$ at a transverse and preferably acute angle, e.g., 20°±10°, relative to a line normal L to the lower surface 16 of the bone plate 10.

As shown in FIGS. 2 and 3, according to a preferred aspect of the invention, the system also includes the single type of bone screw 24 that can be used in either the threaded screw hole 18 or non-threaded compression screw holes 20, 22 to (i) mechanically lock relative to the plate when the screw is inserted into the threaded locking hole, or (ii) axially load the plate 10 relative to bone when the screw is inserted into the compression screw holes. The screw 24, as described below, operates as a standard locking screw when inserted into the threaded screw hole 18. However, when inserted into the round or oblong compression screw holes 20, 22, the screw 24 has structure that mates with the screw seats 34, 54 (FIGS. 8 and 10) thereof to allow the screw to apply significant axial load to the plate without plastic deformation of the screw. This is significant, as plastic deformation could result in metal debris which could lead to tissue irritation at the implant site. Further, significant plastic deformation could result in welding of the screw to the plate, rendering removal of the screw and/or plate—if necessary—a difficult and potentially dangerous procedure.

Figure 6:
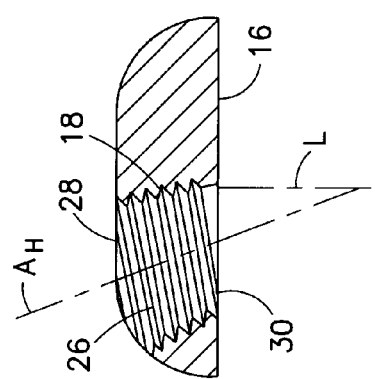
FIG. 6 is a section view along line 6-6 in FIG. 3.
Figure 11:
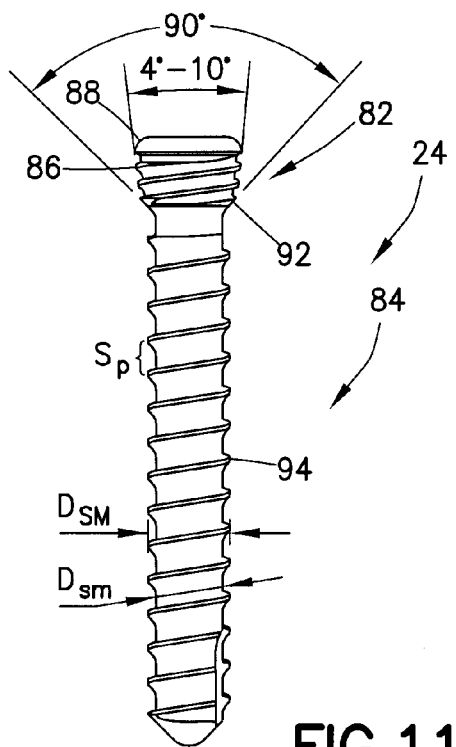
FIG. 11 is a side elevation view of a bone screw according to the invention.

Turning to FIG. 11, the screw 24 has a head 82 and a shaft 84. The head 82 includes conically tapered external threads 86 terminating in an upper peripheral rim 88 at the trailing end of the threads that functions as a stop. The threads 86 preferably taper at 4°-10° per side, more preferably at 6° per side. The head 82 also includes a driver engagement socket 90 for receiving a torque driver tool with a corresponding shape. By way of example, the socket 90 may define a square or hexagonal cross-section (FIG. 6). According to a preferred aspect of the invention, at the transition of the head 82 to the shaft 84, a bearing annulus 92 is provided. The bearing annulus 92 is smaller than the threaded portion of the head and forms a preferably smooth 90° conical portion. The angle of the lower surface of the bearing annulus 92 presents a large surface area for the given diameter of the annulus and is advantageous in supporting high axial loads on the screw seats 34, 54 of the compression holes. Further, the bearing annulus 92 displaces the axially loads from the weaker portions of the screw head, particularly at the thinnest portion of the wall of the screw head between the driver socket 90 and the external threads 86, which could otherwise cause the screw to plastically deform and potentially fail.

The shaft 84 has bone engaging threads 94 which define a shaft major diameter $D_{SM}$, a shaft minor diameter $D_{Sm}$, a shaft thread pitch $S_P$. The shaft thread pitch $S_P$ is approximate to, but greater than, the thickness $T_R$ of the vertical walls 44, 64 of the compression screw holes 20, 22. The shaft major diameter $D_{SM}$ is larger than the second diameter $D_2$ (FIG. 7) of the round compression screw hole 20 (as well as the corresponding second minor diameter $D_{m2}$ of the oblong compression screw hole 22, FIG. 9). More particularly, the dimensions of the shaft 84 of the screw equate to the second diameter $D_2$ of the round compression screw hole, as follows:

$$D_2 = \frac{(D_{SM} + D_{Sm})}{2} + \text{up to 4\% for clearance.}$$

Figure 12:
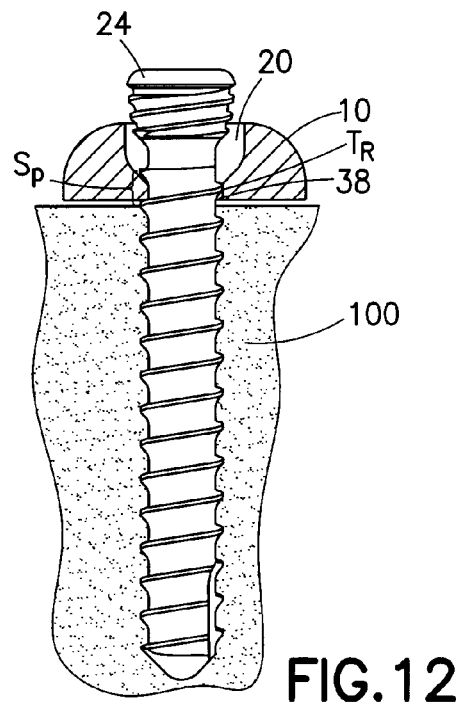
FIG. 12 shows a partial section view of the bone screw of the invention being partially inserted into the bone plate and bone.
Figure 13:
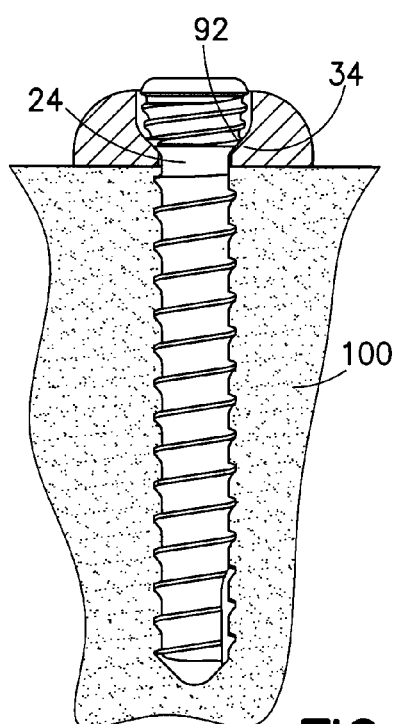
FIG. 13 is a view similar to FIG. 12, showing full insertion of the bone screw into the bone plate and bone.
Figure 14:
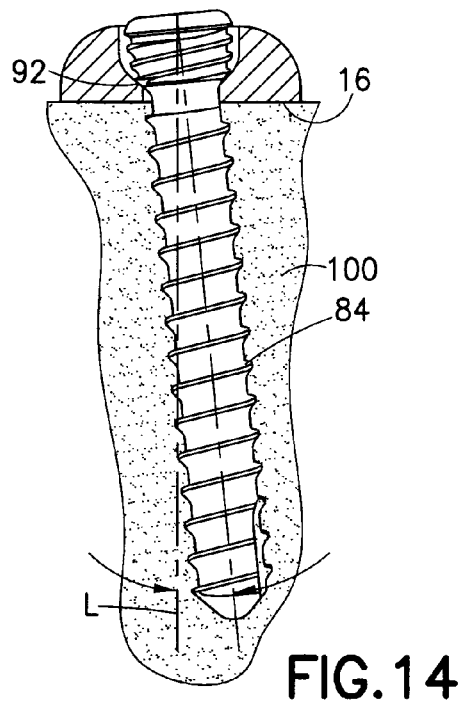
FIG. 14 is a view similar to FIG. 13, showing full angled insertion of the bone screw into the bone plate and bone.

Turning to FIG. 12, in view of the relationship of the dimensions of the components, the shaft 84 of the screw must be rotationally thread through the lowermost opening 38 of the compression screw hole 20 to be longitudinally advanced therethrough. This is transparent to the user, as the screw shaft 84 is being simultaneously threaded through bone 100. Referring to FIG. 13, when the screw 24 is advanced such that the bearing annulus 92 of the head contacts the screw seat 34, further torqueing of the screw causes the load to be carried on the screw at the bearing annulus. As shown in FIG. 14, the compression screw hole can also accommodate approximately 2°-3° of lateral angulation of the shaft 84 on each side of line normal L to the lower surface 16 of the plate (for a total of 4°-6° of angular variability). The screw is inserted within the oblong screw hole in the same manner. However, the oblong screw hole provides the option to adjust the longitudinal displacement of the plate relative to the screw before the screw is fully loaded against the plate.

The holes 18, 20, 22 and screw 24 are structured for clustering together on the bone plate. The screw head, with the bearing annulus 92 located distally of the head threads 86, is of a particularly compact design. This permits more screw holes 18, 20, 22 sized to accommodate the screw to be formed in the plate 10 to provide the surgeon with greater flexibility of screw placement into a bone. In addition, referring to FIG. 3, the screw holes 18, 20, 22 can be spaced closer together in a cluster 96 to provide the advantages of placement on both plates of large and relatively small dimensions. In such a cluster 96, a threaded hole 18 is located substantially equidistantly between two compression screw holes, and more preferably between a round compression screw hole 20 and an oblong compression screw hole 22. Such a cluster 96 preferably provides screw hole spacing in a dense pattern, wherein portions of each of a threaded hole 18 and the both types of the compression holes 20, 22 are located within a bounding area bounded by a circle preferably no larger than twice the diameter $D_U$ of the upper opening 28 of the threaded hole 18 (as shown at bounding area $BA_1$) or more preferably 1.5 diameters of the diameter $D_U$ of the upper opening 28 of the threaded hole 18 (as shown at bounding area $BA_2$) in FIG. 3. Further, each of the clusters as well as the indicated bounding areas preferably also includes a portion of at least one of the guidewire holes 23. Multiple clusters 96 of screw holes are preferably provided to the bone plate.

Figure 9:
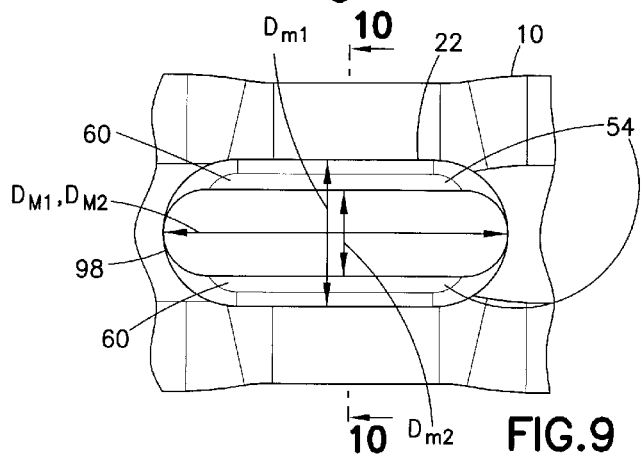
FIG. 9 is a top view of a small portion of the bone plate showing an oblong compression screw hole according to the invention.
Figure 10:
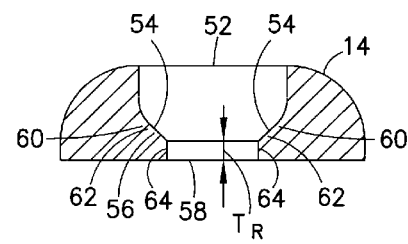
FIG. 10 is a section view of the bone plate across line 10-10 in FIG. 9.

In one method of use, referring to FIGS. 9-11, the plate is positioned on the bone at a location suited for stabilization of the fracture. A hole is drilled through an oblong compression hole 22 in the plate and into the underlying bone, and a screw 24 is inserted into the hole. As indicated above, as (i) the major diameter $D_{SM}$ of the screw shaft is larger than the second minor diameter $D_{m2}$ (or transverse dimension of the slot) of the compression screw hole 22, (ii) the minor diameter $D_{Sm}$ of the screw shaft is smaller than the second minor diameter $D_{m2}$, and (iii) the vertical wall thickness $T_R$ of the rails 60 defining the lowermost portion of the compression slot is smaller than the pitch $S_P$ of the shaft thread, the screw shaft can and must be rotatably threaded through the wall portion 64 to advance the shaft 84 through the compression hole. Once the screw is advanced into the bone such that the screw head 82 is proximate the screw seat 54 (but not fully loaded against the plate) the plate 10 may be translated relative to the screw 24. With the screw shaft threads 94 engaging the bone, the screw 24 is then driven to load the bearing annulus 92 against the screw seat 54 and thereby force the plate 10 and the bone against each other. With as little as 5-6 in-lbs torque, 120 lbs of axial load can be generated between the bearing annulus 92 and the seat 54 with no load on or damage to the screw head threads 86.

Before or after tightening the screw through the oblong compression hole, additional holes are drilled into the bone through the round compression holes and/or the locking holes (FIG. 1-3). For all holes drilled through the round compression holes and into the underlying bone, respective screws are inserted through such holes and driven against the plate to load the plate against the bone, as described with respect to the oblong compression holes, without the option to translate the plate prior to final loading. As shown in FIG. 14, such screws may be inserted into the compression screw holes (round and oblong) with angular variability of up to 2°-3° per side, within a plane transverse to the longitudinal axis of the slot of the screw hole and across both rails of the screw hole. Even at such angles, the bearing annulus 92 support the loads placed thereon without plastic deformation of the head. Turning to FIG. 6, for all holes drilled through the threaded holes 18 and into the underlying bone, the shaft 84 is advanced through the threaded screw hole into an underlying drilled hole and the screw head 82 is threaded into locking engagement with the internal threads 26 of the screw hole. The shaft threads 94 retain bone and bone fragments 100 beneath the plate 10 and hold such bone and fragments in a stable and preferably fixed position relative to the plate.

Turning back to FIG. 9, in another method of use, the design of the screw seat 54 of the oblong compression holes 22, with no seat portion located in alignment with the first and second major diameters $D_{M1}$, $D_{M2}$, permits the oblong compression hole to be used in application of dynamic compression across a fracture. In dynamic compression, the plate is initially secured to the bone with one or more screws 24 only at one side of a fracture. Then, on the other side of the fracture, a screw 24 is inserted at the end of an oblong screw hole located further from the fracture. Because the oblong compression screw hole has no seat along its first and second major diameters $D_{M1}$, $D_{M2}$, the shaft 84 of the screw can be closely approximated to the indicated 'further' end without interference with a screw seat. The screw shaft 84 is advanced into the bone at such location until the bearing annulus 92 of the head 82 of the screw 24 abuts the upper edge, e.g., at edge 98, of the screw hole. Then, further advancement causes the screw 24 to be longitudinally translated within the slot 66 of screw hole toward the screw seat 54 so that the bearing annulus 92 can be seated deeper. As the screw is attached to the bone, this causes the bone portion to which the screw is attached to be displaced in a manner that reduces the fracture. Additional screws can be inserted as necessary to maintain the reduction and complete the fixation.

Referring now to FIGS. 15 and 16, a bone plate system may include a second embodiment of compression screw holes 120 for use in association with the screw 24. The round compression screw hole 120 includes a conically shaped hole 121 with an upper opening 132 with a first diameter and a lower opening 138 with a second diameter. The screw hole is deeper to accommodate the rim 88 of the screw head 82. In distinction from the first embodiment, the round compression hole has a single rail 140 extending from one side thereof below the upper opening 132 to define screw seat 134 and a lower portion 136. The lower opening defines a slot 146 adjacent the rail 140. The second embodiment of the oblong screw hole 122 is of similar design, with one upper diameter larger than an orthogonal upper diameter. The second embodiment of the compression screw holes 120 (, 122) provides for a screw seat 134 for supporting the bearing annulus 92 of the screw 24 only at one side of the screw hole 122. Constraining the angle of the screw by the provision of a conical hole ensures that the bearing annulus applies the load to the screw seat. Further, while only a single rail 140 is provided, the second diameter of the lower opening 138 (or second minor diameter of an oblong compression screw hole) continues to be smaller than the screw shaft major diameter and larger than the screw shaft minor diameter $D_{SM}$ (for reference see FIG. 11). Further, the lower portion 136 defined by the rail 140 has a thickness $T_R$ along vertical wall 144 that is smaller than the pitch $S_P$ of the screw shaft threads. As such, the screw shaft 94 can and must be inserted through the lower opening 138 of the compression hole by rotational advancement.

In all embodiments, the system allows a single type of screw to be used in association with a plate to provide for axial loading of the plate to the bone at compression holes and locking fixation of the screws to the plate at locking holes. Thus, the system reduces the inventory of components required for a surgical plating procedure. Moreover, the system simplifies the procedure, as the surgeon is able to use the same screw regardless of the type of screw fixation required.

The system is particularly well adapted to plates and screws of small dimensions, such as screws at or smaller than 3.5 mm, or more particularly at or smaller than 2.7 mm, and is capable of providing high axial loads, on the order of 120 lbs of axial load, without significant plastic deformation between the screw and plate.

There have been described and illustrated herein embodiments of a bone plating and screw system. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A bone plate for use in stabilizing a fracture of a bone, comprising:
   a bone supporting metal plate having an upper surface, a bone contacting lower surface, and a plurality of screw holes extending between said upper and lower surfaces, said plurality of screw holes including,
   i) a tapered locking screw hole having threads helically arranged about its interior, said locking screw hole having an upper opening with an upper diameter, and a lower opening with a lower diameter, and ii) first and second compression screw holes having an upper opening with a first diameter, and a lower opening with a second diameter smaller than said first diameter in one direction and a third diameter equal to said first diameter in a direction orthogonal to the second diameter, and defining a central axis through the centers of the upper and lower openings, at least one rail extending across a portion of at least one of said compression screw holes to define a screw seat with an angled upper surface, and a vertical wall with a thickness extending in the same dimension as a central axis of the compression screw hole, wherein portions of each of said upper opening of said locking screw hole and said upper openings of said first and second compression screw holes are located within a bounding area bounded by a bounding circle no larger than twice said diameter of said upper opening of said locking screw hole such that said locking screw hole and said first and second compression screw holes are arranged in a cluster.

2. A bone plate according to claim 1, wherein:
said bounding circle is no larger than 1.5 times said diameter of said upper opening of said locking screw hole.

3. A bone plate according to claim 1, wherein:
said locking screw hole is located substantially equidistantly between said first and second compression screw holes.

4. A bone plate according to claim 1, wherein:
at least a portion of a non-threaded cylindrical hole smaller than each of said screw holes and sized for closely receiving a K-wire is provided within said bounding circle.

5. A bone plate according to claim 4, wherein:
said bounding circle is no larger than 1.5 times said diameter of said upper opening of said locking screw hole.

6. A bone plate according to claim 1, wherein:
said cluster comprises a plurality of clusters of screw holes.

7. A bone plate according to claim 1, wherein:
said first and second compression screw holes includes a round compression screw hole and an oblong compression screw hole.

8. A bone plate according to claim 7, wherein:
said plate defines a longitudinal axis, said at least one of said first and second compression screw holes is situated along said longitudinal axis, and said locking screw hole is situated offset from said longitudinal axis.

9. A bone plate according to claim 8, wherein:
said locking screw hole extends along an axis oriented at an acute angle relative to a line normal to said lower surface of said bone plate.

10. A bone plate according to claim 8, wherein:
both of said first and second compression screw holes are situated along said longitudinal axis.

11. A bone plate kit for use in stabilizing a fracture of a bone, comprising:
a) a bone supporting metal plate having an upper surface, a bone contacting lower surface, and a plurality of a screw holes extending between said upper and lower surfaces, said plurality of screw holes including,
i) a tapered locking screw hole having threads helically arranged about its interior, said locking screw hole having an upper opening with an upper diameter, and a lower opening with a lower diameter, and ii) first and second compression screw holes having an upper opening with a first diameter, and a lower opening with a second diameter smaller than said first diameter in one direction and a third diameter equal to said first diameter in a direction orthogonal to the second diameter, and defining a central axis through the centers of the upper and lower openings, at least one rail extending across a portion of at least one of said compression screw holes to define a screw seat with an angled upper surface, and a vertical wall with a thickness extending in the same dimension as a central axis of the compression screw hole, and wherein portions of each of said upper opening of said locking screw hole and said upper openings of said first and second compression screw holes are located within a bounding area bounded by a bounding circle no larger than twice said upper diameter of said upper opening of said locking screw hole such that said locking screw hole and said first and second compression screw holes are arranged in a cluster; and b) a plurality of like bone screws, each having a head and a shaft, for respective insertion into said locking screw hole and at least one of said first and second compression screw holes.

12. A bone plate kit according to claim 11, wherein:
said head of each of said bone screws includes conically tapered external threads, a proximal peripheral rim, a driver engagement socket at a proximal end of said screw head for receiving a torque driver tool, and a lower bearing annulus distal of said external threads, said bearing annulus smaller in diameter than said external threads and defined by a conical surface, and said shaft of each of said bone screws includes bone engaging threads defining a shaft major diameter, a shaft minor diameter, and a shaft thread pitch, wherein, said shaft thread pitch is approximate to, but greater than, said thickness of said vertical wall of said first and second compression screw holes, said shaft major diameter is larger than said second diameter of said first and second compression screw hole, and said shaft minor diameter is smaller than said second diameter of said first and second compression screw holes, wherein, a first of said bone screws can be inserted into said tapered locking screw hole, with said shaft extending through said lower opening of said locking screw hole and said tapered threads of said head of said bone screw engaging said internal threads of said locking screw hole to engage said screw relative to said plate, and a second and third of said bone screws can be respectively rotatably inserted into said first and second compression screw holes in a direction from said upper surface of said plate to said lower surface of said plate to cause said screw shaft of said bone screw to threadedly engage with said plate at said lower opening of the respective of said first and second compression screw holes and into the bone, and as said screw shaft is advanced into the bone, said bearing annulus axially loads against said screw seat of said respective first and second compression screw holes.

13. A bone plate according to claim 12, wherein:
said plate defines a longitudinal axis, said at least one of said first and second compression screw holes is situated along said longitudinal axis, and said locking screw hole is situated offset from said longitudinal axis.

14. A bone plate according to claim 13, wherein:
said locking screw hole extends along an axis oriented at an acute angle relative to a line normal to said lower surface of said bone plate.

15. A bone plate according to claim 13, wherein:
both of said first and second compression screw holes are situated along said longitudinal axis.

16. A bone plate kit for use in stabilizing a fracture of a bone, comprising:
   a) a bone plate having an upper surface, a bone contacting lower surface, and a plurality of a screw holes extending between the upper and lower surfaces, said plurality of screw holes including,
      i) a tapered threaded screw hole having threads helically arranged about its interior, said threaded screw hole having an upper opening with a upper diameter, and a lower opening with a lower diameter, and
      ii) a round compression screw hole having an upper opening with a first diameter, and a lower opening with a second diameter smaller than said first diameter in one direction and a third diameter equal to said first diameter in a direction orthogonal to the second diameter, and defining a central axis through the centers of said upper and lower openings,
      at least one rail extending across a portion of said round compression screw hole to define a screw seat with an angled upper surface, and a vertical wall with a thickness extending in the same dimension as a central axis of said round compression screw hole, and
      iii) an oblong compression screw hole having an upper opening with a first major diameter and a first minor diameter, and a lower opening with a second major diameter equal to the first major diameter and a second minor diameter smaller than said first minor diameter, and defining a central axis through the centers of the upper and lower openings,
      at least one rail extending across a portion of said oblong screw hole to define a screw seat with an angled upper surface, and a vertical wall with a thickness extending in the same direction as a central axis of said oblong screw hole,
      wherein portions of each of said upper openings of said locking screw, said round compression screw hole, and said oblong compression screw hole are located within a bounding area bounded by a bounding circle no larger than twice said diameter of said upper opening of said locking screw hole such that said locking screw hole, said round compression screw hole, and said oblong compression screw are arranged in a cluster.

17. A bone plate according to claim 16, wherein:
said bounding circle is no larger than 1.5 times said diameter of said upper opening of said locking screw hole.

18. A bone plate according to claim 16, wherein:
said locking screw hole is located substantially equidistantly between said first and second compression screw holes.

19. A bone plate according to claim 16, wherein:
at least a portion of a non-threaded cylindrical hole smaller than each of said screw holes and sized for closely receiving a K-wire is provided within said bounding circle.

20. A bone plate according to claim 19, wherein:
said bounding circle is no larger than 1.5 times said diameter of said upper opening of said locking screw hole.

21. A bone plate according to claim 19, wherein:
said cluster comprises a plurality of clusters of screw holes.

22. A bone plate according to claim 16, wherein:
said plate defines a longitudinal axis, said at least one of said round compression screw hole and said oblong compression screw hole is situated along said longitudinal axis, and said tapered threaded screw hole is situated offset from said longitudinal axis.

23. A bone plate according to claim 22, wherein:
said tapered threaded screw hole extends along an axis oriented at an acute angle relative to a line normal to said lower surface of said bone plate.

24. A bone plate according to claim 22, wherein:
both of said round compression screw holes and said oblong compression screw hole are situated along said longitudinal axis.

25. A bone plate according to claim 16, in combination with a plurality of like bone screws, each having a head and a shaft and configured for insertion into said tapered threaded, round compression, and oblong compression screw holes.

26. A bone plate for use in stabilizing a fracture of a bone, comprising:
   a bone supporting metal plate having an upper surface, a bone contacting lower surface, and defining a longitudinal axis, and a plurality of a screw holes extending between said upper and lower surfaces, said plurality of screw holes including,
      i) a tapered locking screw hole having threads helically arranged about its interior, said locking screw hole having an upper opening with an upper diameter, and a lower opening with a lower diameter, said tapered locking screw located offset from said longitudinal axis and extending along an axis oriented at an acute angle relative to a line normal to said lower surface of said bone plate, and
      ii) a round compression screw hole having an upper opening with a first diameter, and a lower opening with a second diameter smaller than said first diameter in one direction and a third diameter equal to said first diameter in a direction orthogonal to the second diameter, and defining a central axis through the centers of said upper and lower openings, and
      iii) an oblong compression screw hole having an upper opening with a first major diameter and a first minor diameter, and a lower opening with a second major diameter equal to the first major diameter and a second minor diameter smaller than said first minor diameter, and defining a central axis through the centers of the upper and lower openings,
      at least one of said round compression screw hole and said oblong compression screw hole being situated along said longitudinal axis,
      wherein portions of each of said upper openings of said locking screw, said round compression screw hole, and said oblong compression screw hole are located within a bounding area bounded by a bounding circle no larger than twice said diameter of said upper opening of said locking screw hole such that said locking screw hole, said round compression screw hole, and said oblong compression screw are arranged in a cluster.

27. A bone plate according to claim 26, wherein:
said bounding circle is no larger than 1.5 times said diameter of said upper opening of said locking screw hole.

28. A bone plate according to claim 26, wherein:
said tapered locking screw hole is located substantially equidistantly between said round and oblong compression screw holes.

29. A bone plate according to claim 26, wherein:
at least a portion of a non-threaded cylindrical hole smaller than each of said screw holes and sized for closely receiving a K-wire is provided within said bounding circle.

30. A bone plate according to claim 26, wherein:
each of said round compression screw hole and said oblong compression screw hole are situated along said longitudinal axis.

* * * * *